(12) United States Patent
Petteys (10) Patent No.: US 9,750,613 B2
(45) Date of Patent: Sep. 5, 2017

(54) STABILIZED TOTAL ANKLE PROSTHESIS (71) Applicant: Wright Medical Technology, Inc., Arlington, TN (US)

(72) Inventor: Christine M. Petteys, Bartlett, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 246 days.

(21) Appl. No.: 13/674,504

(22) Filed: Nov. 12, 2012

(65) Prior Publication Data
US 2014/0135939 A1 May 15, 2014

(51) Int. Cl.
*A61F 2/42* (2006.01)
*A61F 2/30* (2006.01)
*A61F 2/28* (2006.01)

(52) U.S. Cl.
CPC ........ *A61F 2/4202* (2013.01); *A61F 2/30767* (2013.01); *A61F 2002/2892* (2013.01); *A61F 2002/30003* (2013.01); *A61F 2002/30004* (2013.01); *A61F 2002/3011* (2013.01); *A61F 2002/3013* (2013.01); *A61F 2002/30013* (2013.01); *A61F 2002/3065* (2013.01); *A61F 2002/30116* (2013.01); *A61F 2002/30164* (2013.01); *A61F 2002/30387* (2013.01); *A61F 2002/30654* (2013.01); *A61F 2002/30662* (2013.01); *A61F 2002/30878* (2013.01); *A61F 2002/30889* (2013.01); *A61F 2002/4205* (2013.01); *A61F 2002/4207* (2013.01)

(58) Field of Classification Search
CPC ................................. A61F 2/4202–2002/4207
USPC ....................................................... 623/21.18
See application file for complete search history.

(56) References Cited

U.S. PATENT DOCUMENTS

| | | | | | |
|---|---|---|---|---|---|
| 3,798,679 | A | * | 3/1974 | Ewald | 623/20.31 |
| 4,156,944 | A | * | 6/1979 | Schreiber et al. | 623/21.18 |
| 6,039,763 | A | * | 3/2000 | Shelokov | A61F 2/4425 623/17.16 |
| 7,625,409 | B2 | | 12/2009 | Saltzman et al. | |
| 2004/0073311 | A1 | * | 4/2004 | Ferree | A61F 2/442 623/17.14 |
| 2004/0133276 | A1 | * | 7/2004 | Lang | A61F 2/30756 623/14.12 |
| 2005/0192673 | A1 | | 9/2005 | Saltzman et al. | |
| 2006/0036325 | A1 | * | 2/2006 | Paul | A61B 17/1757 623/17.14 |
| 2008/0195212 | A1 | * | 8/2008 | Nguyen | A61F 2/4425 623/17.16 |
| 2010/0087927 | A1 | * | 4/2010 | Roche et al. | 623/19.11 |
| 2011/0035019 | A1 | * | 2/2011 | Goswami et al. | 623/21.18 |
| 2013/0204375 | A1 | * | 8/2013 | Winslow | A61F 2/40 623/19.13 |

* cited by examiner

*Primary Examiner* — Yashita Sharma
*Assistant Examiner* — Rebecca Preston
(74) *Attorney, Agent, or Firm* — Duane Morris LLP (57) ABSTRACT

The present invention relates to a stabilized ankle prosthesis configured for use in patients with compromised soft tissue in the ankle. The prosthesis of the present invention is a two-component design comprising a stabilizing lip configured to constrain movement in the general direction of compromised soft tissue.

16 Claims, 5 Drawing Sheets

STABILIZED TOTAL ANKLE PROSTHESIS

BACKGROUND OF THE INVENTION

An ankle joint may become severely damaged and painful due to arthritis from prior ankle surgery, bone fracture, infection, osteoarthritis, posttraumatic osteoarthritis or rheumatoid arthritis, for example. Options for treating the injured ankle have included anti-inflammatory and pain medications, braces, physical therapy, amputation, joint arthrodesis, and total ankle replacement.

In the past the main-stay of ankle arthrosis has been joint arthrodesis, due to the poor prosthetic survival rate of total ankle replacements. This is primarily due to the clinical results of early ankle designs. Therefore, arthrodesis has been the only choice for many surgeons and patients. Arthrodesis improves stability and reduces pain, but also severely inhibits normal function of the ankle joint. Although some patients have very good results from ankle fusion, surrounding joints above and below the fusion may become arthritic and painful because the lack of ambulation places additional stress on these joints.

There have been numerous ankle joint replacement prostheses developed over the last 30 years. The Agility ankle is an example of an early implant design. It is comprised of two components—one part is cemented to the tibia and the other part is cemented to the talus. An issue with the design of the early ankle prostheses is that although they allow for some dorsiflexion/plantarflexion motion, the articulation surfaces restrict varus/valgus and rotation motions. Another problem surrounding early implant designs is their reliance on the surrounding soft tissues of the ankle to stabilize the implant. As a result, they are not well suited for implantation in individuals with compromised soft tissues.

Another example is the Salto Talaris ankle device, which is a fixed-bearing ankle prosthesis. This two-component ankle system utilizes a conical talar component with two different radii of curvature and a curved groove in the sagittal plane. The medial radius is smaller than the lateral to allow equal tensioning of the collateral ligaments. The tibial component is designed for a fixed insertion of a polyethylene bearing piece that is replaceable. Some issues with the fixed-bearing prostheses include high wear rate of the articulation surfaces, ambulatory constraint, and loosening of the implant.

Another ankle replacement device is the Scandanavian Total Ankle Replacement (STAR). In this device the tibial component is designed for less bone resection and has two parallel bars for insertion into the subchondral bone. The talar component is meant to mimic the talar dome and has a central ridge for stabilization of a polyethylene piece. The STAR prosthesis inhibits inversion/eversion coupling with plantarflexion/dorsiflexion motion. This leads to straining and potential damage to the deltoid ligaments on the medial side of the ankle. Another issue with this device is edge loading, which puts a great amount of stress on the ridge of the implant and results in the implant retracting from the talus.

More modern designs have attempted to increase the range of motion while maintaining the integrity of the surrounding soft tissues of the ankle. For example, U.S. Pat. No. 7,625,409 discloses a prosthesis designed to allow full range of motion while minimizing edge loading and subsidence. However, this prosthesis fails to address the need for an implant for use in patients with compromised soft tissues in the ankle.

DETAILED DESCRIPTION OF THE INVENTION

Although detailed embodiments of the present invention are disclosed herein, it is to be understood that the invention is not restricted to the details of the embodiments. Many changes in design, composition, configuration and dimensions are possible without departing from the spirit and scope of the instant invention. Further, the figures are not necessarily to scale. Some features may be exaggerated to show details of particular components. Specific structural and functional details disclosed herein are not to be interpreted as limiting, but as an aid for teaching one skilled in the art how to variously employ the present invention. Accordingly, it should be readily understood that the embodiments described and illustrated herein are illustrative only, and are not to be considered as limitations upon the scope of the present invention.

An ankle joint is a very complex joint having three motions that occur simultaneously: dorsiflexsion/plantarflexion, varus/valgus, and internal/external rotation. In a healthy ankle, the ankle joint relies on soft tissues, including ligaments, to provide stability. These tissues include, for example, an anterior inferior tibiofibular ligament, a calcaneal-fibular ligament, a posterior talo-fibular ligament, a syndesmotic ligament, an anterior capsule of the ankle joint (which helps keep the ankle from anterior movement), and a deltoid ligament. These soft tissues contribute to the overall function of the ankle by ensuring joint stability.

In a healthy ankle these ligaments naturally stretch according to specific ankle motions in order to keep the joint secure. It is desirable that an ankle replacement prosthesis prevents stretching these ligaments beyond their natural range of motion. Further, because the ankle joint absorbs a stress greater than four times the body's weight with every step, an ankle replacement prosthesis ideally will be able to withstand the pressures associated with weight-bearing and motion.

In a patient with healthy soft tissue in the ankle, this tissue will provide stability to a prosthesis. However, when the soft tissue is compromised, a prosthesis can fail for various reasons, including instability. Therefore, there exists a need for an implant that provides ambulation of the ankle joint similar to that of a natural ankle and that remains stable when implanted in a patient with compromised soft tissues.

An ankle prosthesis 1 of the present invention addresses these and additional problems. Ankle prosthesis 1 of the present invention provides adequate range of motion for the primary degrees of freedom of the talar joint, including movement in a frontal plane and a sagittal plane. Additionally, ankle prosthesis 1 of the present invention provides stability for implantation into an ankle joint with compromised soft tissues by constraining movement in the general direction of compromised soft tissues.

Figure 1:
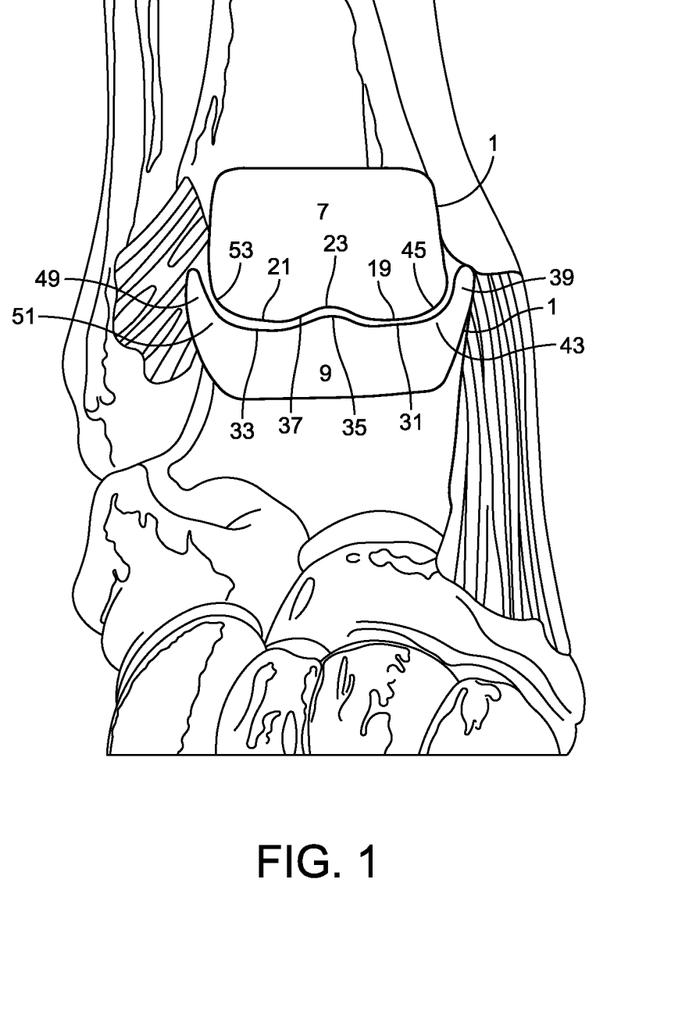
FIG. 1 shows an anterior view of an ankle prosthesis according to an embodiment of the present invention.
Figure 2:
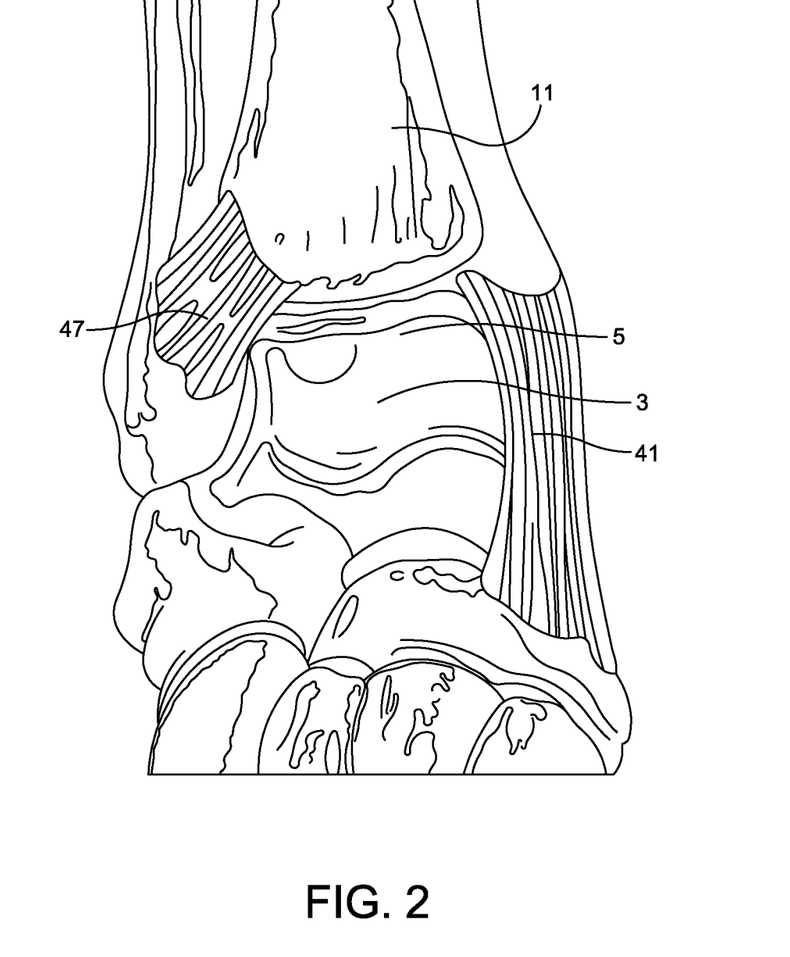
FIG. 2 shows an anterior view of an ankle joint and surrounding soft tissues.

As may be seen with reference to FIG. 2, the natural anatomy of a talus bone 3 has a bicondylar contour 5. The ankle prosthesis of the present invention comprises a talar component and a tibial component. In one embodiment, the talar component mimics the natural anatomy of the talus bone and the tibial component comprises a complimentary contour. In another embodiment depicted in FIG. 1, the natural anatomy is mimicked in a reverse orientation, where a bicondylar contour is on a tibial component 7 and a talar component 9 comprises a complimentary contour.

Figure 3:
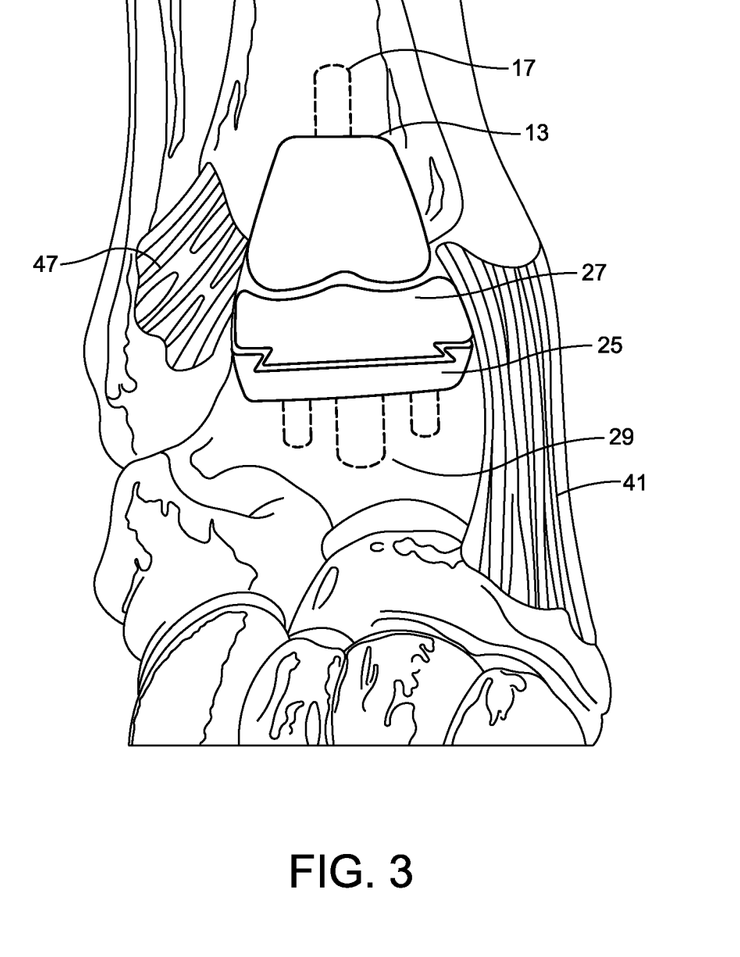
FIG. 3 shows an anterior view of exemplary means of attachment of an ankle prosthesis according to an embodiment of the present invention.

In one embodiment of the present invention, ankle prosthesis 1 comprises a two-component design which is sufficiently sized to prevent subsidence. With reference to FIG. 1, ankle prosthesis 1 comprises tibial component 7 and talar component 9. Tibial component 7 is configured for attachment to a tibia 11. As may be seen in FIG. 3, tibial component 7 comprises an attachment surface 13 positioned on a proximal portion of tibial component 7 and an articulation surface 15 positioned on a distal portion of tibial component 7, wherein at least a portion of attachment surface 13 is configured for attachment to tibia 11. The attachment surface and the articulation surface of tibial component 7 may comprise a unitary piece, or in an alternative embodiment the surfaces may be two distinct units attached to one another by any suitable means of attachment.

Tibial component 7 may be attached to tibia 11 by any suitable means of attachment, e.g., one or more screws or one or more rods. An exemplary means of attachment 17 may be seen with reference to FIG. 3. In one embodiment, tibial component 7 functions as the "male" component of ankle prosthesis 1. For example, referring to FIGS. 1 and 3, articulation surface 15 of tibial component 7 comprises at least one convex contour 19 extending anteriorly-posteriorly on a medial portion of tibial component 7, at least one convex contour 21 extending anteriorly-posteriorly on a lateral portion of tibial component 7, and at least one concave contour 23 extending anteriorly-posteriorly in a sagittal plane of tibial component 7. In this embodiment, articulation surface 15 comprises a bicondylar contour which mimics the natural anatomy of the proximal portion of talus bone 3. Radii of curvature of the at least one convex contour 19 on the medial portion and the at least one convex contour 21 on the lateral portion of articulation surface 15 of tibial component 13 may be the same, or in an alternative embodiment a radius of curvature of the medial portion may be greater, or in another embodiment a radius of curvature of the lateral portion may be greater.

In an alternative embodiment, tibial component 7 functions as the "female" component of ankle prosthesis 1. In this embodiment articulation surface 15 of tibial component 7 comprises at least one concave contour extending anteriorly-posteriorly on a medial portion of tibial component 7, at least one concave contour extending anteriorly-posteriorly on a lateral portion of tibial component 7, and at least one convex contour extending anteriorly-posteriorly in a sagittal plane of tibial component 7. In this embodiment, articulation surface 15 comprises a contour which is complimentary to a bicondylar contour. Radii of curvature of the at least one concave contour on the medial portion and the at least one concave contour on the lateral portion of articulation surface 15 of tibial component 13 may be the same, or in an alternative embodiment a radius of curvature of the medial portion may be greater, or in another embodiment a radius of curvature of the lateral portion may be greater.

Complimentary talar component 9 is configured for attachment to talus 3. Talar component 9 comprises an attachment surface 25 on a distal portion of the component and an articulation surface 27 on a proximal side of the component. At least a portion of attachment surface 25 is configured for attachment to talus 3. The attachment surface and the articulation surface of talar component 9 may comprise a unitary piece, or in an alternative embodiment the surfaces may be two distinct units attached to one another by any suitable means of attachment.

Talar component 9 may be attached to talus 3 by any suitable means of attachment, e.g., one or more screws or one or more rods. An exemplary means of attachment 29 may be seen with reference to FIG. 3. Articulation surface 27 of talar component 9 is configured to compliment articulation surface 15 of tibial component 7, and accordingly may comprise the "female" or "male" component of ankle prosthesis 1 depending on the configuration of tibial component 7. Articulation surface 27 of talar component 9 comprises a contour for receiving articulation surface 15 of tibial component 7. In one embodiment of the present invention in which talar component 9 comprises the "female" component of ankle prosthesis 1, articulation surface 27 of talar component 9 has at least one concave contour 31 extending anteriorly-posteriorly on a medial portion of talar component 9, at least one concave contour 33 extending anteriorly-posteriorly on a lateral portion of talar component 9, and at least one convex contour 35 extending anteriorly-posteriorly on a sagittal plane of talar component 9. Convex contour 35 is configured to compliment the at least one concave contour 23 on the sagittal plane of articulation surface 15 of tibial component 7. At least one concave contour 31 on medial portion of articulation surface 27 of talar component 9 is configured to compliment the at least one convex contour 19 on the medial portion of articulation surface 15 of tibial component 7 and the at least one concave contour 33 on the lateral portion of articulation surface 27 of talar component 9 is configured to compliment the at least one convex contour 21 on the lateral portion of articulation surface 15 of tibial component 7. Radii of curvature of the at least one concave contour 31 on the medial portion of talar component 9 and the at least one concave contour 33 on the lateral portion of talar component 9 may be the same, or in an alternative embodiment a radius of curvature on the medial portion may be greater, or in another embodiment a radius of curvature of the lateral portion may be greater.

In an alternative embodiment, talar component 9 comprises the "male" component of ankle prosthesis 1. In this embodiment, articulation surface 27 of talar component 9 has at least one convex contour extending anteriorly-posteriorly on a medial portion of talar component 9, at least one convex contour extending anteriorly-posteriorly on a lateral portion of talar component 9, and at least one concave contour extending anteriorly-posteriorly on a sagittal plane of talar component 9. Concave contour is configured to compliment the at least one convex contour on the sagittal plane of articulation surface 15 of tibial component 7. At least one convex contour on medial portion of articulation surface 27 of talar component 9 is configured to compliment the at least one concave contour on the medial portion of articulation surface 15 of tibial component 7, and the at least one convex contour on the lateral portion of articulation surface 27 of talar component 9 is configured to compliment the at least one concave contour on the lateral portion of articulation surface 15 of tibial component 7. Radii of curvature of the at least one convex contour on the medial portion of talar component 9 and the at least one convex contour 33 on the lateral portion of talar component 9 may be the same, or in an alternative embodiment a radius of curvature on the medial portion may be greater, or in another embodiment a radius of curvature of the lateral portion may be greater.

Articulation surface 15 of tibial component 7 and articulation surface 27 of talar component 9 form an articulation interface 37. Congruence of the articulation surfaces is maintained in all positions of an ankle joint movement, including dorsiflexion/plantarflexion, inversion/eversion, and internal/external rotation.

In order to maintain congruence of the articulation surfaces of prosthesis 1 when implanted in an ankle with compromised soft tissue, one embodiment of the present invention comprises a lip on the female component. The lip is configured to maintain congruence of the articulation surfaces in patients having compromised soft tissues by at least partially limiting mobility in a direction toward the compromised soft tissue. Congruence of the articulation surfaces may be maintained when the articulation surfaces correspond to one another and are in agreement for each direction of motion.

In one embodiment of the present invention, a lip 39 is configured to stabilize prosthesis 1 when implanted in patients with compromised soft tissues on a medial side of the ankle. For example, lip 39 may be configured for implantation in a patient with a compromised deltoid ligament 41 (depicted in FIG. 2 with talar component 9 being the "female" component). In this embodiment, lip 39 comprises a raised surface on a medial edge 43 of articulation surface 27 of talar component 9 such that the raised surface extends to a position which is in superior relation to a medial edge 45 of articulation surface 15 of tibial component 7. In this embodiment, the raised surface constrains movement in a medial direction, or eversion of the implant. In an alternative embodiment in which tibial component 7 is the "female" component, the lip comprises a raised surface on a medial edge of articulation surface of tibial component 7 such that the raised surface extends to a position which is in inferior relation to a medial edge of the articulation surface of talar component 9 (not depicted).

In another embodiment of the present invention, the lip is configured to stabilize prosthesis 1 when implanted in patients with compromised soft tissues on a lateral side of the ankle, such as a compromised anterior inferior tibiofibular ligament 47 (depicted in FIG. 2), for example. In this embodiment, a lip 49 comprises a raised surface on a lateral edge 51 of talar component 9 such that the raised surface extends to a position which is in superior relation to a lateral edge 53 of articulation surface 15 of tibial component 7. In this embodiment, the raised surface constrains movement in a lateral direction, or inversion of the implant. In an alternative embodiment in which tibial component 7 is the "female" component, the lip comprises a raised surface on a lateral edge of articulation surface of tibial component 7 such that the raised surface extends to a position which is in inferior relation to a lateral edge of the articulation surface of talar component 9 (not depicted).

In another embodiment, prosthesis 1 is provided for implantation in patients with compromised soft tissues on both the medial and lateral sides of the ankle. In this embodiment, the lip comprises a first raised surface 39 on medial edge 43 of talar component 9 such that the raised surface extends to a position which is in superior relation to medial edge 45 of articulation surface 15 of tibial component 7 and a second raised surface 49 on lateral edge 51 of talar component 9 such that the raised surface extends to a position which is in superior relation to lateral edge 53 of articulation surface 15 of tibial component 7. In this embodiment, varus/valgus freedom of movement is constrained, but there is freedom of movement for dorsiflexion/plantarflexion. In an alternative embodiment, tibial component 7 is the "female" component and comprises the lip.

Figure 4:
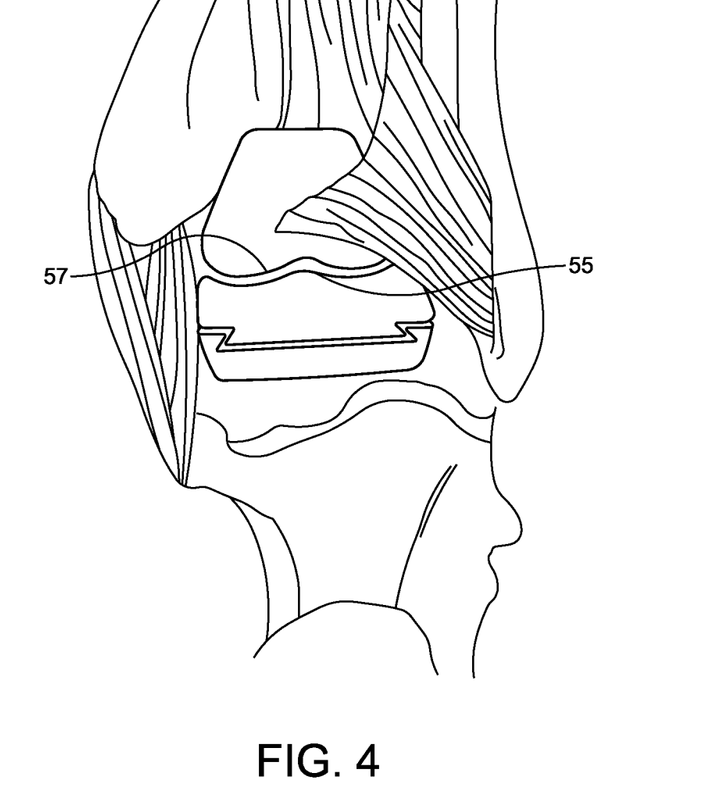
FIG. 4 shows a posterior view of an ankle prosthesis according to an embodiment of the present invention.
Figure 5:
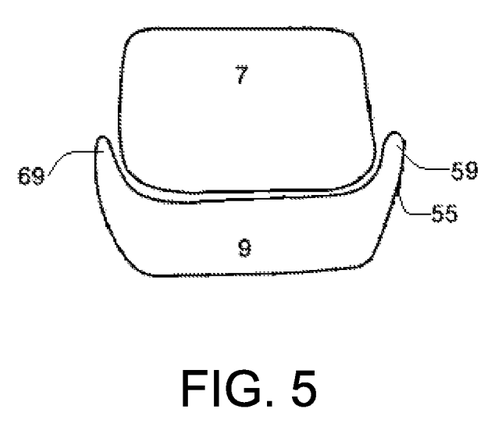
FIG. 5 shows a medial view of an ankle prosthesis according to an embodiment of the present invention.

With reference to FIGS. 4 and 5, in another embodiment prosthesis 1 is provided for implantation in patients with compromised soft tissue on a posterior side of the ankle In this embodiment, the lip comprises a raised surface (see FIG. 5) on a posterior edge 55 of the talar component 9 such that the raised surface extends to a position which is in superior relation to a posterior edge 57 of articulation surface 15 of tibial component 7. In this embodiment, posterior displacement of tibial component 7 is prevented. In an alternative embodiment, tibial component 7 is the "female" component and comprises the lip to prevent posterior displacement of talar component 9.

The lips may also be configured for implantation in patients with compromised soft tissue on an anterior side of the ankle In this embodiment, the lip comprises a raised surface (see FIG. 5) on an anterior edge of talar component 9 such that the raised surface extends to a position which is in superior relation to an anterior edge of articulation surface 15 of tibial component 7. In this embodiment, anterior displacement of tibial component 7 is prevented. In an alternative embodiment, tibial component 7 is the "female" component and comprises the lip to prevent anterior displacement of talar component 9.

In another embodiment, prosthesis 1 is provided for implantation in patients with compromised soft tissue such that stabilization of the implant and constraint of movement is necessary in more than one direction of mobility. The lip comprises a raised surface (not shown) extending from medial edge 43 of articulation surface 27 of talar component 9 posteriorly curving to lateral edge 51 of articulation surface 27 of talar component 9 and continuing around returning to medial edge 43. The lip extends to a position which is in superior relation to articulation surface 15 of tibial component 7. In this configuration, the lip comprises a general cup-like contour providing stabile implantation in patients with more severe soft tissue impairment. In an alternative embodiment, tibial component 7 is the "female" component and comprises the cup-like lip.

Another consideration for providing a successful total ankle replacement prosthesis is the material or materials of construction. In order to reduce wearing of the components, and therefore failure of the prosthesis, it is desirable to use a material, or a combination of materials, which create minimal friction between the two components. Suitable materials include those which minimize friction and resultant wear of the articulation surfaces. Some exemplary materials include a metal, a polymer, or a ceramic material. However, other suitable materials are contemplated within the spirit and scope of the present invention. In one embodiment of the present invention, articulation surface 15 of tibial component 7 is comprised of a first material and articulation surface 27 of talar component 9 is comprised of a second material. The first material and the second material may be substantially the same. In an alternative embodiment, the first and second material are substantially different. Further, tibial component and talar component are each comprised of an attachment surface and an articulation surface. The articulation surface and attachment surface of tibial component 7 may comprise materials which are substantially the same, or in an alternative embodiment the surfaces may comprise materials which are substantially different. Likewise, the articulation surface and attachment surface of talar component 9 may comprise materials which are substantially the same, or in an alternative embodiment the surfaces may comprise materials which are substantially different.

Additionally, it may be desirable to use a material which promotes osseointegration, so that a direct interface between attachment surface 25 of talar component 9 and talus 3, and in between attachment surface 13 of tibial component 7 and tibia 11, are formed. To this end, one embodiment of the present invention comprises a material of construction which promotes osseointegration. For example, the material may comprise pores into which osteoblasts and supporting tissues can migrate.

What is claimed is:

1. An ankle prosthesis comprising:
    an attachment surface on a proximal portion adapted to fit into a recess in a resected tibia, and an articulation surface on a distal portion, the body having two side surfaces which angle toward each other such that the articulation surface is wider than the attachment surface;
    a talar component configured for attachment to a talus, comprising a flat attachment surface on a distal portion and an articulation surface on a proximal portion;
    wherein the articulation surface of the tibial component comprises a medial portion and a lateral portion, the medial portion having a first convex contour, the lateral portion having a second convex contour, wherein a first concave contour is located between the first and second convex contours;
    wherein the articulation surface of the talar component comprises a medial portion and a lateral portion, the medial portion having a second concave contour, the lateral portion having a third concave contour, wherein a third convex contour is located between the second and third concave contours, and the articulation surface of the talar component is configured to complement the articulation surface of the tibial component; and
    wherein the articulation surface of the talar component comprises a lip configured to maintain congruence of the articulation surface of the tibial component with the articulation surface of the talar component, wherein the lip comprises raised surfaces curving around each of the medial portion of the articulation surface of the talar component, the lateral portion of the articulation surface of the talar component, a posterior edge of the articulation surface of the talar component and an anterior edge of the articulation surface of the talar component, forming a cup-like contour.

2. The ankle prosthesis of claim 1, wherein the raised surface on the medial portion of the articulation surface of the talar component is in superior relation to the third convex contour of the articulation surface of the talar component and is configured to limit eversion.

3. The ankle prosthesis of claim 1, wherein the raised surface on the lateral portion of the articulation surface of the talar component is in superior relation to the third convex contour and is configured to limit inversion.

4. The ankle prosthesis of claim 1, wherein the raised surface on the medial portion of the articulation surface of the talar component is in superior relation to the third convex contour and is configured to limit eversion, and the raised surface on the lateral portion of the articulation surface of the talar component is in superior relation to the third convex contour and is configured to limit inversion.

5. The ankle prosthesis of claim 1, wherein the lip is configured to limit posterior displacement of the tibial component.

6. The ankle prosthesis of claim 1, wherein the lip is configured to limit anterior displacement of the tibial component.

7. The ankle prosthesis of claim 1, wherein the lip comprises a first raised surface on the posterior edge of the articulation surface of the talar component, wherein the first raised surface is configured to limit posterior displacement of the tibial component, and a second raised surface on the anterior edge of the articulation surface of the talar component, wherein the second raised surface is configured to limit anterior displacement of the tibial component.

8. The ankle prosthesis of claim 1, wherein one of the raised surfaces of the lip of the articulation surface of the talar component extends from a medial edge curving posteriorly to a lateral edge and continuing around returning to the medial edge, wherein the lip is configured to provide stability to the prosthesis.

9. The ankle prosthesis of claim 1, wherein the articulation surface of the tibial component is comprised of a first material and the articulation surface of the talar component is comprised of a second material.

10. The ankle prosthesis of claim 9, wherein the first and second material are substantially the same.

11. The ankle prosthesis of claim 9, wherein the first and second material are substantially different.

12. The ankle prosthesis of claim 1, wherein the tibial component has a bicondylar contour.

13. An ankle prosthesis comprising:
    a tibial component configured for attachment to a tibia, comprising an attachment surface on a proximal portion of the tibial component and an articulation surface on a distal portion of the tibial component, wherein the articulation surface of the tibial component has a bicondylar contour comprising a medial portion and a lateral portion, the medial portion having a first convex contour, the lateral portion having a second convex contour, wherein a first concave contour is located between the first and second convex contours;
    a talar component comprising a proximal portion and a distal portion, wherein:
        the proximal portion of the talar component has an articulation surface and a trapezoid-shaped projection opposite the articulation surface,
        the distal portion of the talar component has an attachment surface configured for attachment to a talus, the distal portion of the talar component having a trapezoid-shaped groove opposite the attachment surface, the trapezoid-shaped groove configured to slidably receive the trapezoid-shaped projection of the proximal portion of the talar component,
        the articulation surface of the talar component is configured to complement the bicondylar contour of the tibial component and comprises a medial portion and a lateral portion, the medial portion having a second concave contour, the lateral portion having a third concave contour, wherein a third convex contour is located between the second and third concave contours, and
        the articulation surface of the talar component comprises a lip having raised surfaces curving around each of the medial portion of the articulation surface of the talar component, the lateral portion of the articulation surface of the talar component, a posterior edge of the articulation surface of the talar component and an anterior edge of the articulation surface of the talar component, forming a cup-like contour.

14. The ankle prosthesis of claim 13, wherein the attachment surface of the tibial component and the attachment surface of the distal portion of the talar component comprise pores adapted to promote osseointegration.

15. The ankle prosthesis of claim 13, wherein the articulation surface of the talar component comprises a first material, the attachment surface of the talar component comprises a second material, and the first material and second material are different from each other.

16. The ankle prosthesis of claim 13, wherein the trapezoid-shaped projection is wider at a distal side of the projection than at a proximal side of the projection.

* * * * *

UNITED STATES PATENT AND TRADEMARK OFFICE
CERTIFICATE OF CORRECTION

PATENT NO. : 9,750,613 B2
APPLICATION NO. : 13/674504
DATED : September 5, 2017
INVENTOR(S) : Christine M. Petteys It is certified that error appears in the above-identified patent and that said Letters Patent is hereby corrected as shown below:

In the Claims

In Claim 1, Lines 2-7 that now reads: "an attachment surface on a proximal portion adapted to fit into a recess in a resected tibia, and an articulation surface on a distal portion, the body having two side surfaces which angle toward each other such that the articulation surface is wider than the attachment surface;"

Should read: --a tibial component configured for attachment to a tibia, comprising a body having an attachment surface on a proximal portion adapted to fit into a recess in a resected tibia, and an articulation surface on a distal portion, the body having two side surfaces which angle toward each other such that the articulation surface is wider than the attachment surface;--.

Signed and Sealed this
Twelfth Day of March, 2019

Andrei Iancu
*Director of the United States Patent and Trademark Office*